United States Patent [19]

Ferrari

[11] Patent Number: 4,605,008

[45] Date of Patent: Aug. 12, 1986

[54] ACOUSTICAL IMAGING SYSTEM

[75] Inventor: Leonard A. Ferrari, San Clemente, Calif.

[73] Assignee: The Regents of the University of California, Berkeley, Calif.

[21] Appl. No.: 667,380

[22] Filed: Nov. 1, 1984

[51] Int. Cl.⁴ .............................................. A61B 10/00
[52] U.S. Cl. .................................................... 128/660
[58] Field of Search .............................. 128/660–663; 73/602

[56] References Cited

U.S. PATENT DOCUMENTS 4,512,196  4/1985  Barnes ............................ 128/660 X

*Primary Examiner*—Kyle L. Howell
*Assistant Examiner*—Francis J. Jaworski
*Attorney, Agent, or Firm*—Poms, Smith, Lande & Rose

[57] ABSTRACT

A method and apparatus is disclosed which improves the image quality obtained in a system for displaying frequency demodulated acoustic images of an object. A squelch signal is added to the input of a frequency demodulator. When the "echo signal" represents merely high frequency noise input to the demodulator, the squelch signal overrides the noise. A uniform level is thereby provided to the image display devices of the system which substantially improves output image quality.

11 Claims, 3 Drawing Figures

ACOUSTICAL IMAGING SYSTEM

FIELD OF THE INVENTION

In general, the present invention relates to the production of images using acoustical signals, and in particular, to an improvement to a system which uses frequency demodulation of ultrasound signals to generate an image of a media supporting acoustic pulse propagation.

BACKGROUND OF THE INVENTION

The scattering properties of tissue are such that amplitude and instantaneous frequency deviations are induced in the backscattered echo signals. The instantaneous frequency of the ultrasound signal is defined as the time rate of change of the signal's phase. Most conventional ultrasound systems generate images based upon amplitude fluctuations in the ultrasonic waves reflected from the tissue. While the amplitude variations induced by the tissue are useful for determining the boundaries of various body organs and also provide some textural information, instantaneous frequency variations induced by the tissue lead to some frequency demodulated images that may be more useful than amplitude demodulated images in characterizing the textural information.

In U.S. Pat. No. 4,543,826 to the common assignee herein, there is disclosed a system for displaying acoustic images made of an object using said instantaneous frequency deviation information.

Acoustical images are generated by frequency demodulating an electrical signal having frequency deviations corresponding to the scattering properties of a media supporting acoustic pulse propagation against which the signal is projected. The system includes a transmitter which generates a signal at a defined frequency, which signal is then transformed into an acoustic pressure signal and projected against the media by a transducer. The transducer also receives acoustic pressure signals reflected from the media. A receiver coupled to the transducer transforms the reflected acoustic pressure signals into electrical signals which are then frequency demodulated. The demodulated signal contains instantaneous frequency deviations responsive to the scattering properties of the media. The frequency demodulated signal may be processed by circuitry to generate a video signal, which is then algorithmically processed by a scan converter and displayed on a video screen. The frequency demodulation may be done by a conventional demodulator, by a V-demodulator, or any other frequency demodulation process. The frequency demodulated signal may also be combined with an amplitude demodulated image signal. Frequency demodulated and amplitude demodulated signals may be used to provide color images of the media.

Accordingly, it is the primary object of the present invention to improve the quality of the images of a media obtained from a system which uses frequency demodulation of ultrasonic waves to obtain the images.

It is another object of the present invention to provide a method to improve the video output image quality in a system using a frequency demodulation technique to generate acoustical images of the media.

A further object of the present invention is to improve the acoustic images of media utilizing the instantaneous frequency deviations of signals derived from reflected ultrasonic waves.

It is a further object of the present invention to provide an improvement to the acoustical imaging system as disclosed in U.S. Pat. No. 4,543,826 by suppressing the effects of low level signals or noise signals on the video images obtained in the practice of that system.

SUMMARY OF THE INVENTION

The present invention, in a broad aspect, provides an improvement to a system for generating an electrical signal having instantaneous frequency deviations corresponding to the scattering properties of a media supporting acoustic pulse propagation, such as a body organ. In general, the system includes a transmitter which generates a signal at a defined frequency, which is then transformed by a transducer into an ultrasonic acoustic pressure signal. The transducer projects the acoustic pressure signal against the media and receives reflected acoustic pressure signals from the media. The transducer transforms the relected acoustic pressure signals into electrical signals which are amplified by a receiver. A frequency demodulator circuit, coupled to the receiver, frequency-demodulates the electrical signal from the receiver to produce a frequency demodulated signal corresponding to the scattering properties of the object. Components and appropriate circuitry visually displays the acoustic images.

The improvement according to the present invention is the addition of a squelch signal to the reflected acoustic pressure signal prior to the frequency demodulation of the reflected acoustic pressure signal. This squelch signal suppresses low-level signals or noise in the reflected acoustic pressure signal and thereby enhances the visual images of the body organ.

Other objects, features, and advantages of the present invention will become apparent from a consideration of the following detailed description and the accompanying drawings.

DETAILED DESCRIPTION OF THE INVENTION

Figure 1:
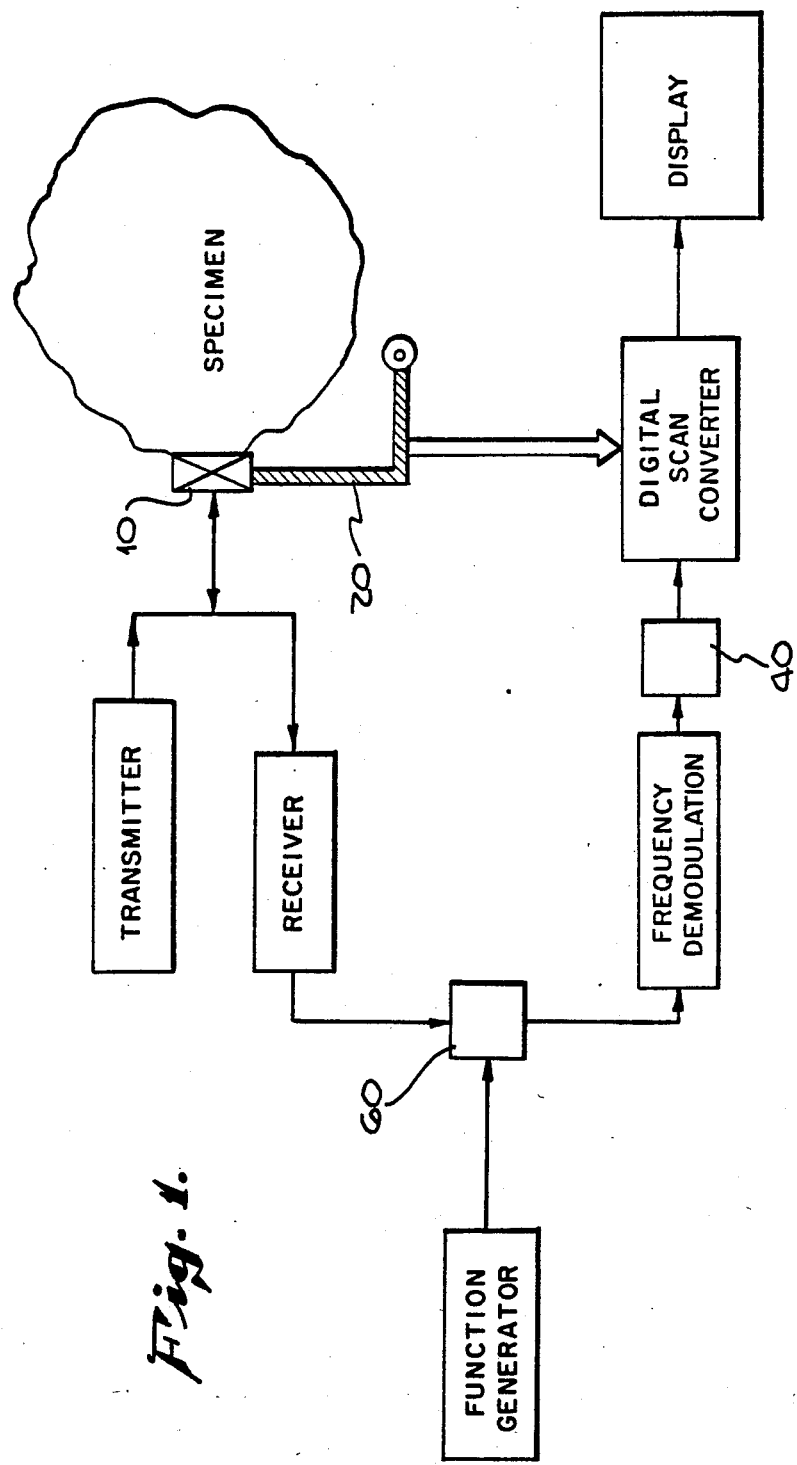
FIG. 1 is a schematic diagram of one embodiment of an improved acoustic imaging system according to the present invention and employing frequency demodulation.
Figure 2:
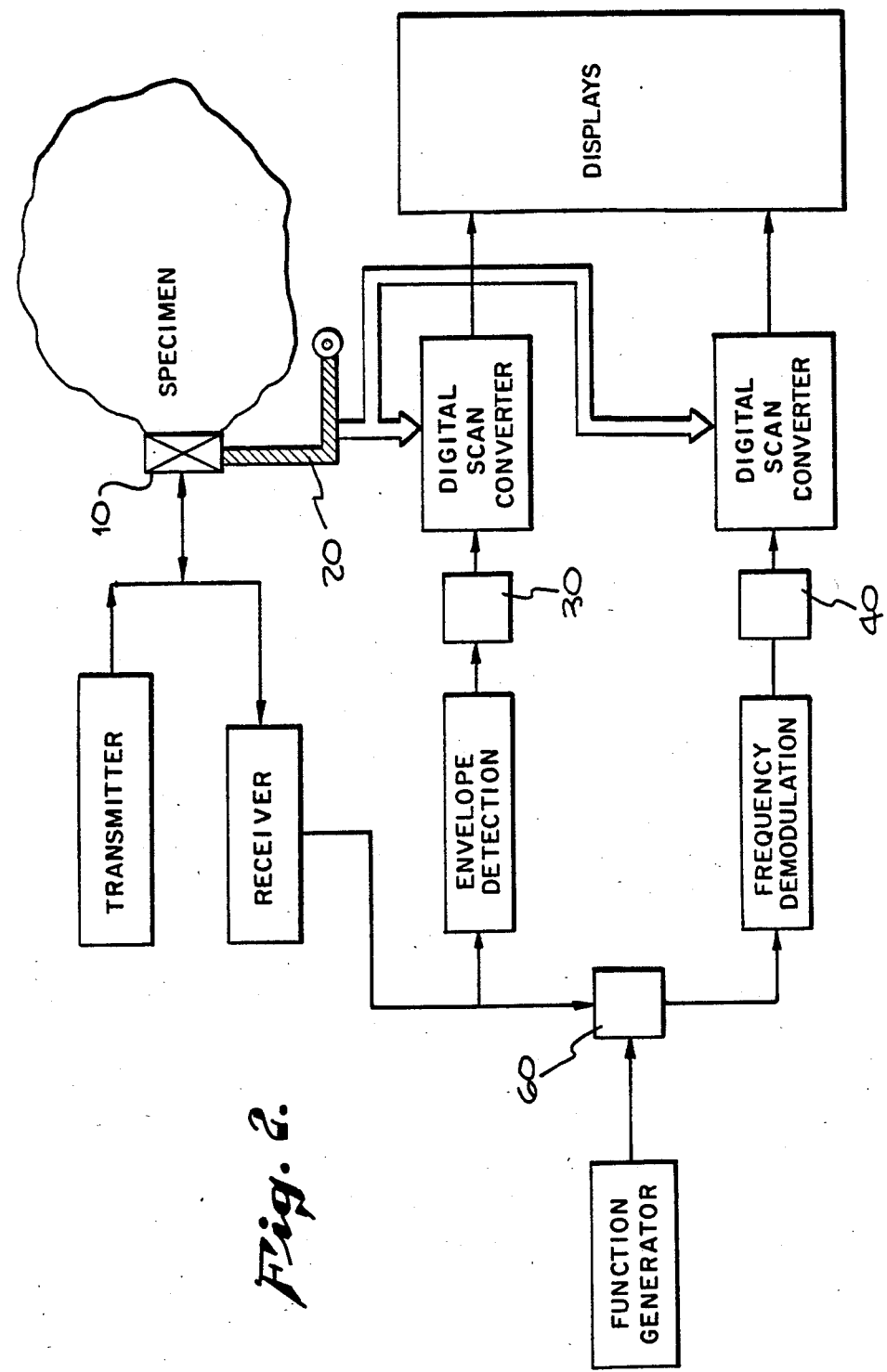
FIG. 2 is a schematic diagram of another improved embodiment of an acoustic imaging system according to the present invention and employing both frequency demodulation and amplitude demodulation.
Figure 3:
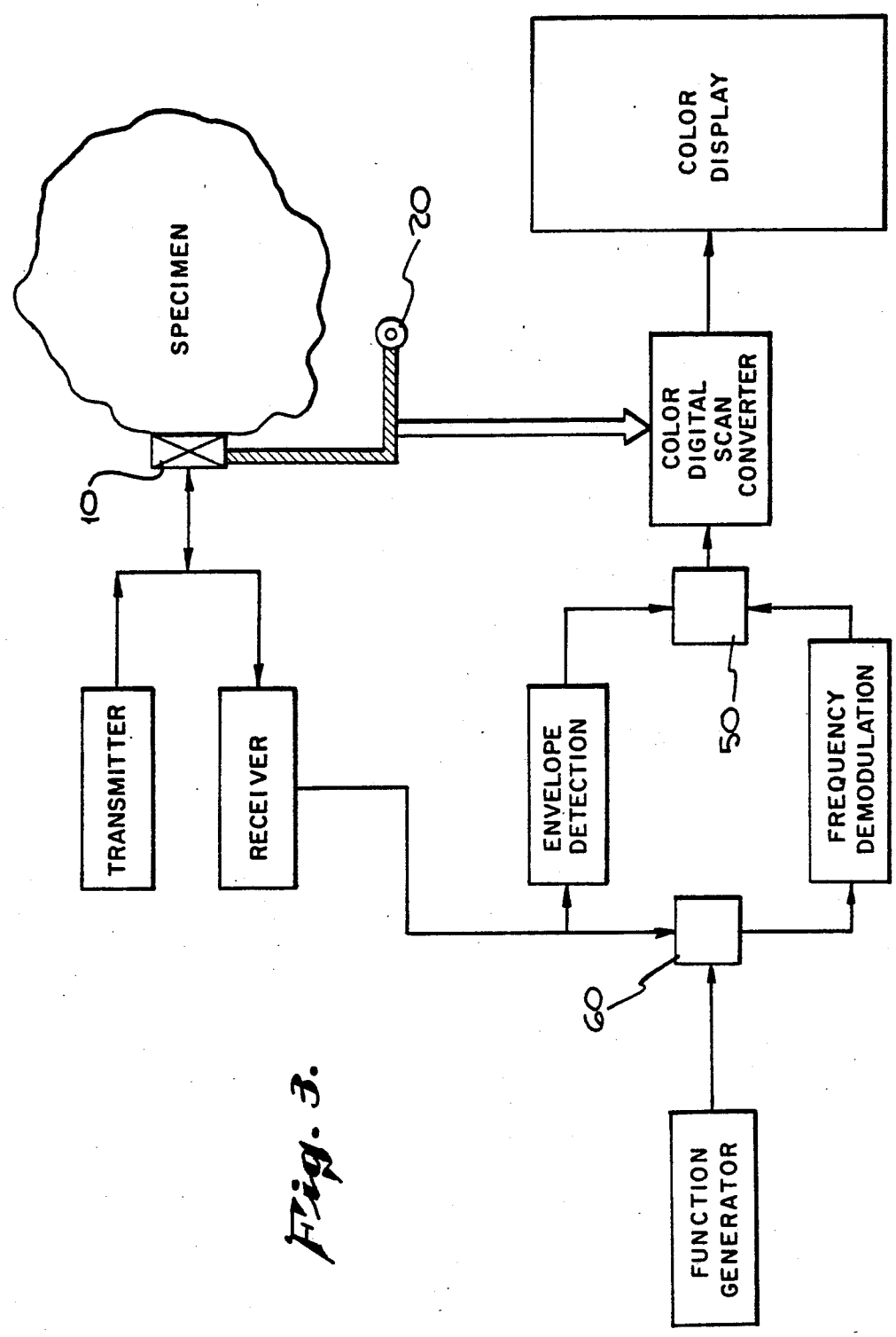
FIG. 3 is a generic schematic diagram of a third improved embodiment of an acoustic imaging system according to the present invention and employing both frequency demodulation and amplitude demodulation to produce color images.

The invention of FIGS. 1, 2 and 3 disclose imaging modalities for ultrasound based upon the carrier crossing fluctuations either by frequency demodulation or by frequency demodulation combined with amplitude demodulation in accordance with U.S. Pat. No. 4,543,826, which is specifically incorporated herein by reference in its entirety.

FIGS. 1, 2 and 3 show the system as set forth in the identified patent, as enhanced with the present invention. As discussed hereinbelow, that enhancement comprises the function generator shown in FIGS. 1, 2, and 3, together with a summing circuit 60. The function generator produces the fixed frequency sine wave signal which suppresses noise or other low-level signals in the received acoustic pressure signal from the receiver in the figures. The function generator which produces the squelch signal can be, for example, a conventional adjustable signal generator having variable frequency and amplitude capabilities, such as a WAVETEK Model 145.

In each of the systems shown in FIGS. 1, 2, and 3, a transmitter generates an electrical pulse which is then transformed into an ultrasonic acoustic pulse by a transducer 10 and projected against the specimen or media, which is usually a body organ. The electrical signal produced by the transmitter is a pulse having a predefined amplitude and a predefined frequency or pulse repetition rate. The transducer 10 is mounted on an arm 20 which is moved relative to the specimen to project the pulse against various portions thereof. The reflections of the ultrasonic pulse from the transmitter generated by the specimen are also detected by the transducer 10 and routed to a receiver as shown in the figures. The receiver transforms the acoustic pressure reflections into an electrical signal for processing by the frequency demodulators shown in the figures. As is also reflected in the figures, the received acoustic pressure signal may also undergo envelope detection in the various sytems. However, the squelch signal is added prior to the frequency demodulation only.

The frequency demodulator shown in the figures is described in detail in U.S. Pat. No. 4,543,826. The frequency demodulator produces a video signal which is sent to the digital scan converter shown in the figures and processed in the manner discussed in the identified patent. As reflected therein, the output of circuit 40 shown in FIGS. 1 and 2 herein is a video signal having acoustic images of the specimen. The output of circuit 50 is a color image of the specimen.

The need for the squelch signal arises from the following fact. The instantaneous frequency deviations which are present in the signal that is reflected from the specimen are converted to positive and negative voltage amplitudes corresponding to positive and negative instantaneous frequency deviations relative to the frequency of the ultrasonic pulse, with the frequency of the ultrasonic pulse producing a zero voltage amplitude.

Whenever the instantaneous value of the rf signal amplitude from the receiver unit is relatively small, that is, for areas of the media which reflect virtually no echo pulses, only a noisy estimate of the instantaneous frequency at the output of the frequency demodulator will be obtained. Hence, when operating under such conditions the system may not discriminate between a true signal return and high frequency noise. It is important to the final video image to have low level echoes transformed into a uniform grey level output in order to provide an accurate picture of the scanned region of interest. It has been found that the addition of a squelch signal in the following prescribed manner solves the high frequency noise problem and provides substantial improvement to the output image quality at the display.

As discussed hereinabove, the present invention adds a squelch signal to the output of the receiver shown in the figures. That squelch signal is produced by the function generator and added to the output of the receiver at a conventional summing circuit 60. In this configuration, the squelch signal captures the frequency demodulator whereby the imput having the largest magnitude controls. Hence, when the receiver output falls below the squelch signal to which it has been added, i.e. when the receiver output signal represents only high frequency signals or noise due to a lack of any substantial echo pulse signals, the output of the demodulator will now be a voltage corresponding to the sine wave input squelch signal.

It has been found that a sine wave squelch signal having a frequency of 2 MHz and an amplitude in the range of 0dB to −20dB below the rf amplitude of the average return signal will provide a uniform gray level output suitable for the display such that regions appearing as high frequency noise are eliminated.

It is to be understood that other design variations are within the scope of the present invention. Accordingly, the present invention is not limited to the particular arrangements which have been illustrated and described in detail herein.

What is claimed is:

1. In a method for generating frequency demodulated acoustic images of a body organ, said method including the steps of generating an electrical signal at a defined frequency, projecting said signal against said organ, receiving the acoustic pressure signals reflected from said organ, frequency demodulating said reflected signals to produce the scattering properties of said organ, and displaying images of said demodulated signal, the improvement comprising:

generating a fixed frequency signal; and adding said fixed frequency signal to said reflected acoustic pressure signals prior to said frequency demodulation such that low-level signals or noise in said reflected acoustic pressure signals is suppressed, whereby said images are enhanced.

2. The method as defined in claim 1, wherein said step of generating said fixed frequency signal comprises:

generating a sine wave signal having a frequency of approximately 2 MHz.

3. The method as defined in claim 2, wherein said step of generating said fixed frequency signal further comprises:

generating said sine wave with an amplitude in the range of 0 to −20 db below the amplitude of said reflected acoustic pressure signal.

4. A method of generating enhanced acoustic images of a body organ, comprising:

generating an electrical signal at a defined frequency;

transforming said signal into an acoustic pulse;

projecting said pulse against said organ;

receiving an acoustic pressure signal reflected from said organ, said acoustic pressure signal having instantaneous frequency deviations corresponding to the scattering properties of said organ;

generating a squelch signal;

adding said squelch signal to said reflected acoustic pressure signal, whereby low-level signals or noise in said reflected acoustic pressure signal is suppressed to enhance said pressure signal;

frequency demodulating said received acoustic pressure signal to produce an electrical signal containing said scattering properties of said organ; and displaying said demodulated signal to produce an image of said organ.

5. The method as defined in claim 2, wherein said step of generating said squelch signal comprises:

generating a sine wave signal having a frequency of approximately 2 MHz.

6. The method as defined in claim 5, wherein said step of generating said squelch signal further comprises:
generating said sine wave with an amplitude in the range of 0 to −20 db below the amplitude of said reflected acoustic pressure signal.

7. An improved system for generating an electrical signal having instantaneous frequency deviations corresponding to the scattering properties of a media supporting acoustic pulse propagation against which said signal is electrically projected, said system having a transmitter for generating a first electrical signal, a transducer for transforming said signal into said acoustic pulse and projecting said pulse into said media, a receiver to transform echo pulse returns into a second electrical signal, and a frequency demodulator for processing said second electrical signal, said improvement comprising:
squelch means, coupled to the output of said receiver, for suppressing low level signals at the input of said frequency demodulator, whereby low level noise effects on said second electrical signal are substantially eliminated.

8. The improvement as defined in claim 7, wherein said squelch means comprises:
signal generator means for variably generating a fixed frequency wave; and
circuit means, coupling said signal generator means to said output of said receiver, for adding said fixed frequency wave to said secondary signal.

9. The improvement as defined in claim 8, wherein said fixed frequency wave comprises:
a sine wave having a frequency of approximately 2 MHz.

10. The improvement as defined in claim 9, wherein said sine wave has an amplitude in the range of 0 to −20 db below the amplitude of said first signal.

11. An improvement to a system for displaying frequency demodulated acoustic images of an object, said system being of the type having: a transmitter for generating a signal at a defined frequency; a transducer for transforming said electrical signal into an ultrasonic acoustic pressure signal, for projecting said acoustic pressure signal against said object, and for receiving acoustic pressure signals reflected from said object in response to said projected acoustic pressure signal; a receiver for transforming said reflected acoustic pressure signal into an electrical signal; a frequency demodulator for frequency demodulating said electrical signal of said receiver to produce a frequency demodulated signal containing instantaneous frequency deviations from said defined frequency responsive to the scattering properties of said object; and means for transforming said frequency demodulated signal into a video signal and for displaying said video signal, said improvement comprising:
signal generator means, for generating a fixed frequency sine wave squelch signal; and
circuit means for adding electrical signals, coupling said signal generator means to the output of said receiver such that said squelch signal captures said frequency demodulated signal, whereby said acoustic images are enhanced.

* * * * *